United States Patent [19]

Levy

[11] Patent Number: 4,568,643

[45] Date of Patent: * Feb. 4, 1986

[54] CONTINUOUS PROCESS FOR PRODUCING N-BUTANOL EMPLOYING ANAEROBIC FERMENTATION

[76] Inventor: Sidney Levy, 4433 Dawn Ave., La Verne, Calif. 91750

[ * ] Notice: The portion of the term of this patent subsequent to Jan. 3, 2001 has been disclaimed.

[21] Appl. No.: 548,615

[22] Filed: Nov. 4, 1983

Related U.S. Application Data

[63] Continuation-in-part of Ser. No. 289,156, Aug. 3, 1981, Pat. No. 4,424,275, which is a continuation-in-part of Ser. No. 76,250, Sep. 17, 1979, abandoned.

[51] Int. Cl.$^4$ .............................................. C12P 7/16
[52] U.S. Cl. ................................... 435/160; 435/801; 435/813
[58] Field of Search ............... 435/160, 813, 801, 161, 435/162

[56] References Cited

U.S. PATENT DOCUMENTS 1,875,536  9/1932  Wheeler et al. ................ 435/161 X
2,389,263  11/1945  Liebmann et al. ............... 435/161 X

OTHER PUBLICATIONS

Rose et al, "The Condensed Chemical Dictionary", Van Nostrand Reinhold Co., 7th Edition (1970), pp. 304–305, 307 and 425–426.

Primary Examiner—R. B. Penland
Attorney, Agent, or Firm—Hopgood, Calimafde, Kalil, Blaustein & Judlowe

[57] ABSTRACT

There is disclosed, in one aspect, a continuous process for producing n-butanol. This process comprises continuously (a) contacting at least one carbohydrate-containing substrate, such as blackstrap molasses, with an n-butanol producing culture, such as *Clostridium acetobutylicum* (Weizmann), in water to effect the fermentation of the substrate and form a product mixture comprising n-butanol, (b) extracting the product mixture from the substrate, culture, and water by forming a solution of the product mixture with an extraction solvent, such as a one or two carbon fluorocarbon, (c) separating the extraction solvent from the product mixture by vaporizing substantially all of the solvent without substantial vaporization of the product mixture, and (d) condensing the vaporized solvent for reuse as an extraction solvent in step (b). In another aspect, there is disclosed an apparatus for conducting such a process. This apparatus comprises (a) means for holding the substrate and water, (b) reactor means for holding the culture and facilitating its contact with the substrate, (c) means for feeding the substrate from the holding means to the reactor means for reaction with the culture to produce the reaction product mixture, (d) extraction means for contacting the reaction product mixture with an extraction solvent to form a solution of the solvent with the product mixture, (e) means for vaporizing the extraction solvent while substantially avoiding the vaporization of the product mixture, and (f) means for condensing the vaporized extraction solvent for reuse.

15 Claims, 9 Drawing Figures

CONTINUOUS PROCESS FOR PRODUCING N-BUTANOL EMPLOYING ANAEROBIC FERMENTATION

CROSS REFERENCE TO RELATED APPLICATION

This application is a continuation-in-part of copending U.S. patent application Ser. No. 289,156, filed Aug. 3, 1981, and entitled "Continuous Process for Producing N-Butanol Employing Anaerobic Fermentation", now U.S. Pat. No. 4,424,275, which, in turn, is a continuation-in-part of now-abandoned U.S. Ser. No. 076,250, filed Sept. 17, 1979, and entitled "Method For Continuous Anaerobic Fermentation of Carbohydrates, Sugars, And The Like To Produce Solvent Materials Such As N-Butanol And Apparatus For The Continuous Anaerobic Fermentation Process." The disclosures of these patent applications are hereby incorporated by reference.

BACKGROUND OF THE INVENTION

Normal (n)-butanol and acetone may be produced by anaerobic fermentation processes as disclosed by Weizmann. Such processes were first commercialized during the period 1914 to 1918. The cultures which were developed and discovered by Weizmann are the anaerobic bacteria *Clostridium Acetobutylicum* Weizmann. Using feed stock materials such as corn and horse chestnuts, these bacteria produce n-butanol and acetone in commerical yields. During World War I, the process was used primarily for obtaining acetone for the manufacture of explosives.

Over the years, improvements were made in the process. There were developed different Clostridium cultures which produced both better yields and different mixtures of solvents including ethanol and propanol. Different feedstock materials such as corn cobs, blackstrap molasses, beet molasses, and others were also used. Furthermore, there were employed other additives as well as nutrients which speeded up the fermentation reaction. The process was operated on a commercial scale until the middle 1950's when cheap petroleum feed stocks as well as processes for making butanol and the other solvents from petroleum became available and petroleum became the primary source for producing butanol.

These fermentation processes have become of greater interest of late due to the recent sharp increase and apparent long term rise in the price of petroleum, coupled with the stable price of farm product feeds for the fermentation. Fermentation products are of current commerical interest as a potential internal combustion fuel to replace the petroleum based fuels. A problem exists, however, with the Weizmann fermentation process because the maximum concentration of butanol is of the order of 2.5% before the bacteria are inactivated. The distillation recovery methods used to separate these solvents require a tremendous amount of energy.

The search has continued for improved processes and apparati for producing n-butanol on a continuous, economical basis. This invention was made as a result of that search.

OBJECTS AND SUMMARY OF THE INVENTION

Accordingly, it is a general object of the present invention to avoid or substantially alleviate the above-noted problems.

A more specific object of the present invention is to provide a continuous process for the production of butanol and other solvents by the anaerobic fermentation of substrates such as sugar and starch-containing agricultural products.

Another object of this invention is to provide an apparatus for continuously passing a fermentation liquor through a stationary culture bed.

It is a further object of this invention to provide a reactor structure which will allow the removal of fermentation products from the fermentation liquor during continuous processing so that the culture medium will not be inactivated.

Still another object of the invention is to provide means for extracting a desired product from a fermentation liquor during the fermentation process without expending substantial energy.

A further object of the invention is to provide a reactor system which will provide for the continuous recycle of a solvent system and fermentation liquor without requiring more than small make-up amounts of water and solvent.

Yet another object of the invention is to provide means for making n-butanol at low cost for use as a fuel for internal combustion engines.

Other objects and advantages of the invention will become apparent from the following summary of the invention and description of its preferred embodiments.

The present invention provides, in one aspect, a continuous process for producing n-butanol from the starting materials of an anaerobic fermentation process. This process comprises (a) continuously contacting at least one carbohydrate-containing substrate with an n-butanol producing culture in water to effect the fermentation of the substrate and form a product mixture comprising n-butanol, (b) continuously extracting the product mixture from the substrate, culture, and water by forming a solution of the product mixture with an extraction solvent while substantially avoiding the formation of a solution of the solvent with the substrate, culture and water, (c) continuously separating the extraction solvent from the product mixture by vaporizing substantially all of the solvent without substantial vaporization of the product mixture, and (d) continuously condensing the vaporized solvent for reuse as an extraction solvent in step (b).

The extraction solvent used in this process is one or more fluorocarbon solvents selected from the group consisting of fluorocarbons that boil at temperatures between −41° C. and +48° C., have vapor pressures at 21° C. between 10 PSIA and 165 PSIA, have heats of vaporization below 60 calories per gram, have a specific heat below 0.28, have a surface tension below 20 dynes per centimeter, have a viscosity below 0.5 centipoise, have a solubility below 1% in water, and have a solubility below 0.2% of water in the fluorocarbon.

In another aspect, the present invention provides an apparatus for conducting a continuous anaerobic fermentation of at least one carbohydrate-containing substrate with a culture to form a reaction product mixture. The apparatus comprises (a) means for holding the substrate and water, (b) reactor means for holding the culture, and facilitating contact between the substrate and culture, (c) means for feeding the substrate from the holding means to the reactor means for reaction with the culture to produce the reaction product mixture, (d) extraction means for contacting the reaction product mixture with an extraction solvent to form a solution of the solvent and product mixture, while substantially avoiding the formation of a solution of the solvent with the substrate, culture, and water, (e) means for vaporizing the extraction solvent while substantially avoiding the vaporization of the product mixture, and (f) means for condensing the vaporized extraction solvent.

BRIEF DESCRIPTION OF THE DRAWINGS

This invention is described further in accordance with the devices, materials, constructions, combinations, and arrangements of parts shown by way of example and illustrated in the accompanying drawings of a preferred embodiment in which.

DESCRIPTION OF THE PREFERRED EMBODIMENTS

Figure 1:
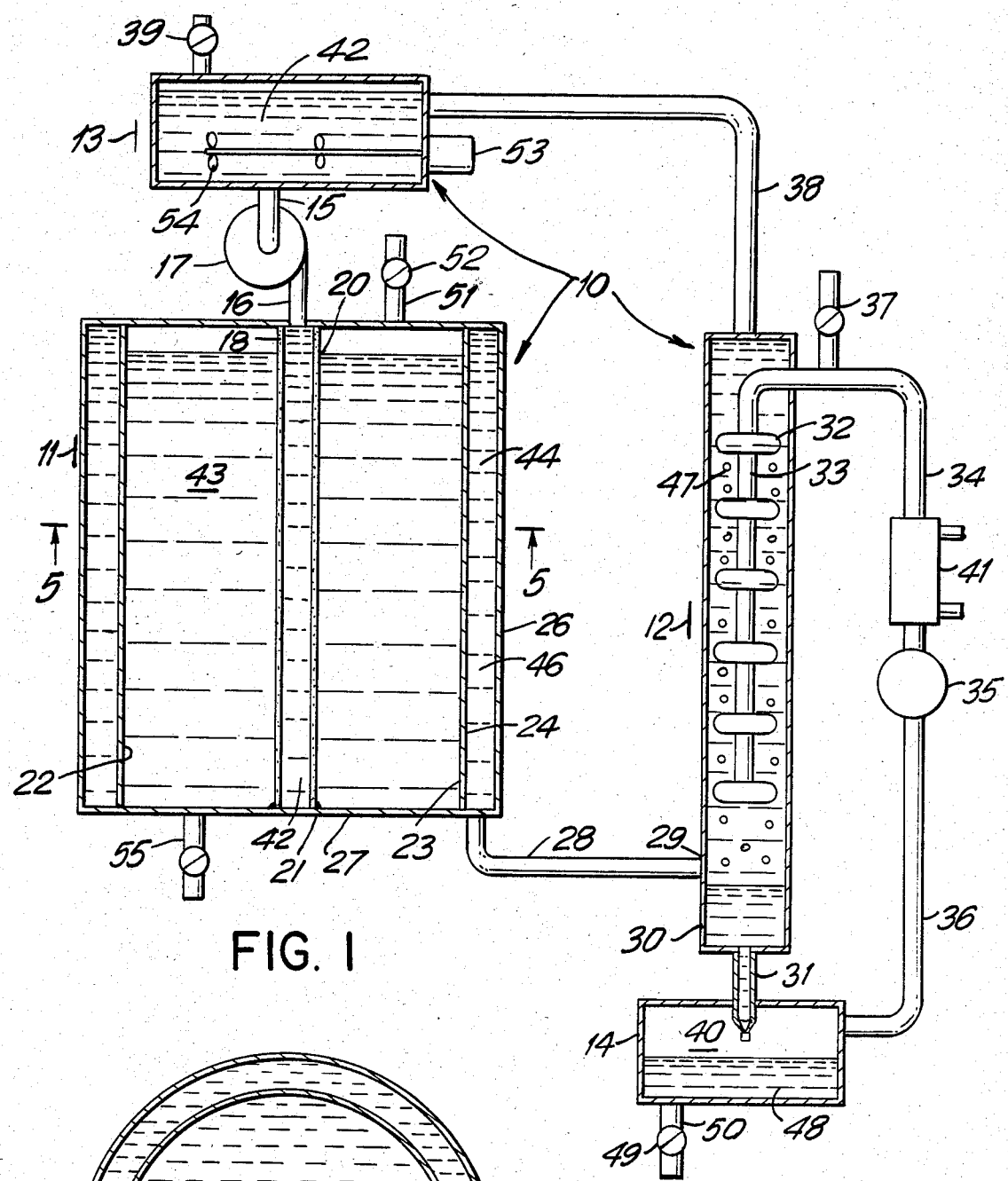
FIG. 1 is an elevation view, partly in section, of a reactor for anaerobic fermentation of carbohydrate and sugar materials.

In the drawings, like parts are designated by like reference numerals throughout.

Figure 3:
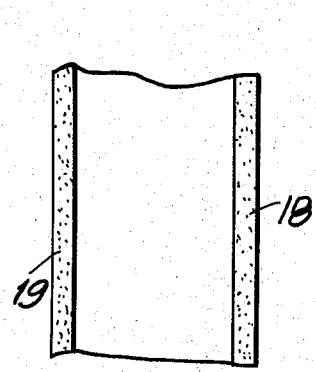
FIG. 3 is an enlargement in section of the central pipe in the main body of the fermentation reactor.

Referring first to FIG. 1, the reference numeral 10 refers to a fermentation system made in accordance with the present invention. The fermentation system comprises four main units: fermentation reactor 11, extraction unit 12, feed tank 13, and extraction separation unit 14. Reactor 11 is connected to feed tank 13 by means of pipe lines 15 and 16 which are connected by pump 17. Pipe line 16 is connected into central distribution pipe 18 of reactor 11. Central distribution pipe 18 has a porous or perforated wall 19 shown in FIG. 3. This perforated or porous wall extends from liquid level 20 (FIG. 1) to reactor bottom 27 at the point designated as 21.

Figure 2:
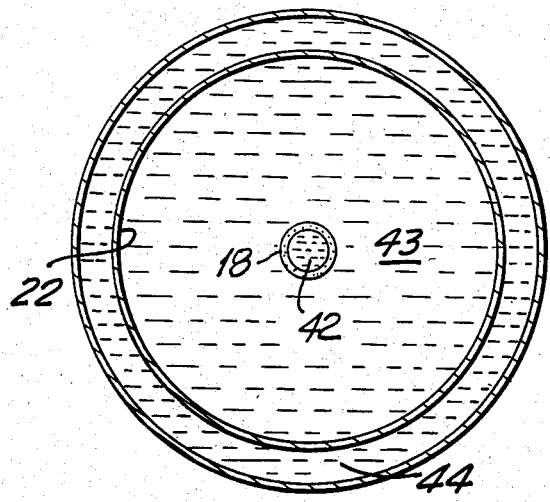
FIG. 2 is a section through the view of FIG. 1 which shows the general arrangement of the flow structure in the main body of the fermentation reactor.
Figure 4:
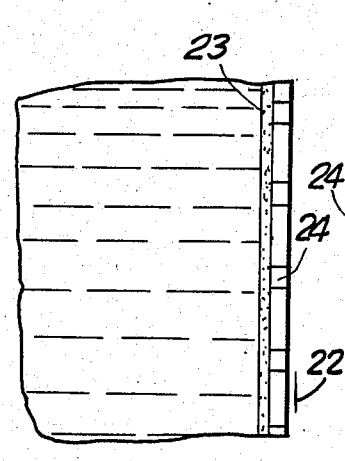
FIG. 4 is a sectional view of the membrane wall of the main fermentation reactor body.
Figure 5:
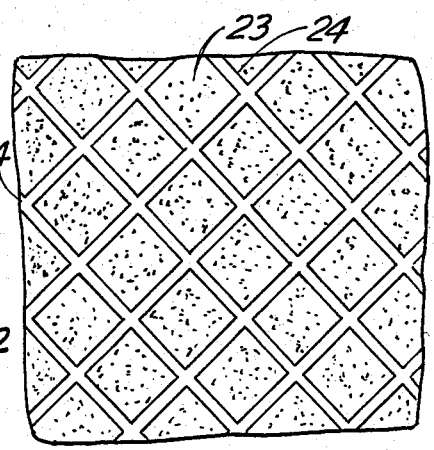
FIG. 5 is a view into the section of FIG. 4 showing the construction of a membrane support.
Figure 8:
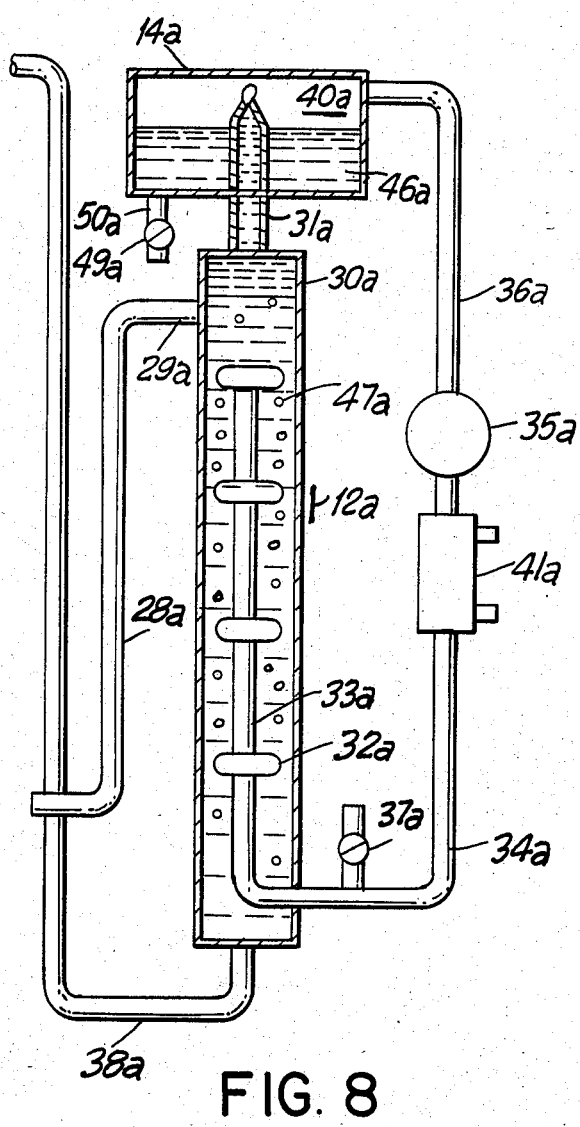
FIG. 8 is an alternative arrangement of the extractor unit using low density extraction solvents.
Figure 6:
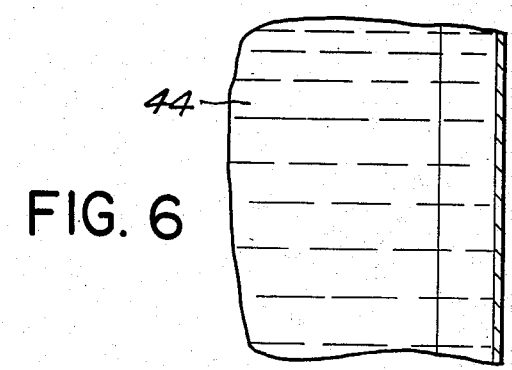
FIG. 6 is an alternative construction of the membrane wall of the fermentation reactor which is designed to reduce the resistance to flow of the fermentation liquor.

FIG. 2 illustrates that reactor 11 comprises several concentric walls. Central distribution pipe 18 is sealed to reactor bottom 27 at the point designated as 21. Membrane wall 22 comprises filter medium 23 as shown in detail in FIG. 4. Filter medium 23 is supported by structural mesh 24 as shown in detail in FIG. 5. Outer wall 26 of reactor 11 is a solid-liquid retaining wall as is reactor bottom 27.

Reactor 11 is connected by means of pipe line 28 to extractor unit 12. The point of entry of pipe line 28 into extractor unit 12 is on the lower portion of extractor body 30, designated as 29. Extraction unit 12 is connected by means of pipe line 31 to extraction separation unit 14 which has a set of injector units 32 attached to standing pipe 33 which runs down unit 12. Standing pipe 33 is connected by pipe line 34 to compressor 35. Compressor 35 is connected by pipe line 36 to extraction separation unit 14. Pipe line 34 has a valved make-up port 37 for introducing additional extraction solvent.

Extraction unit 12 is connected to feed tank 13 by means of pipe line 38. Feed tank 13 is equipped with a valved entry 39 for new fermentation materials. Pipe line 31 which connects extraction unit 12 to extraction separation unit 14 is terminated inside separation unit 14 via nozzle section 40. Pipe line 34 which connects compressor 35 to extraction unit 12 is equipped with cooling condenser 41.

When the unit is in operation, feed tank 13 is filled with a solution of fermentable material 42. The fermentable materials are well known to those skilled in this art. Such materials are carbohydrate-containing and include blackstrap molasses, invert sugar, sucrose, fructose, glucose, wood sugar, xylose, beet molasses, citrus molasses, hydrol, sulfite liquors, saccharified starches, potatoes, corn, wheat, oats, and other fermentable materials well known to those skilled in this art.

This material is pumped by pump 17 into central distribution pipe 18 of reactor 11. Surrounding central distribution pipe 18 and within membrane wall 22 is contained fermentation liquids 43 which include the cultures that cause the fermentation.

These cultures are also well known to those skilled in this art and include *Clostridium acetobutylicum* (Weizmann), *Clostridium butylicum, Clostridium beijerinckii, B. butylaceticum, B. butylicus* B.F., *B. granulobacter pectinovorum*, and others well known to those skilled in this art. Other cultures are set forth in Chapter 13 of *Industrial Microbiology* by Dunn (McGraw Hill, 1959), the disclosure of which is hereby incorporated by reference.

The filter action of filter medium 23 prevents the bacteria in the culture from passing through and retains them in the space between pipe 18 and membrane wall 22. Liquid 44 which passes through membrane wall 22 collects in the space between membrane wall 22 and outer wall 26 and then flows through pipe line 28 into extraction unit 12 at the point designated as 29.

Pump 17 is operated at an appropriate rate to pass the fermentation liquor 43 through reactor 11 at a rate that will cause the fermentation to proceed to a point where somewhat less than the toxification level of butanol is reached in the liquor. This level would be up to about 4%, typically from about 1.5% to about 2% by weight. The exact level would depend upon the specific culture used.

The liquor which enters extraction unit 12 at the point designated as 29 passes up the extraction unit. Countercurrent to the liquor flow, extraction solvent 47 passes in the form of fine droplets generated by exiting from injector units 32. As shown in FIG. 1, it is assumed that the extraction operation is conducted with a solvent which is more dense than the mixture of water, butanol, excess sugars, and other solvents.

The extraction solvents which may be used in this process are set forth in detail in U.S. Pat. No. 4,260,836 to Levy, entitled "Solvent Extraction of Alcohols from Water Solutions With Fluorocarbon Solvents," the disclosure of which is hereby incorporated by reference. These extraction solvents include one or more fluorocarbon solvents that boil at temperatures between −41° C. and +48° C., have vapor pressures at 21° C. between 10 PSIA and 165 PSIA, have heats of vaporization below 60 calories per gram, have a specific heat below 0.28, have a surface tension below 20 dynes per centimeter, have a viscosity below 0.5 centipoise, have a solubility below 1% in water, and have a solubility below 0.2% of water in the fluorocarbon.

Typical fluorocarbon solvents contain one or two carbon atoms and from one to six fluorine atoms with the remainder being hydrogen and chlorine. Such fluorocarbons include difluoro dichloro methane (sold under the trademark FREON-12), monofluoro dichloro methane (FREON-21; ), difluoro monochloro methane (FREON-22), dichloro tetrafluoro ethane (FREON-114), pentafluoro monochloro ethane (FREON-115), 1,1,2-trichloro, 1,2,2-trifluoro ethane (FREON-113), and monofluoro trichloro methane (FREON-11), although other solvents that have the appropriate solvency action and that use relatively small amounts of heat for vaporization may also be used. Mixtures of such extraction solvents may be used in order to maximize various properties.

The physical properties of these fluorocarbon solvents are set forth in detail in Table 1 as follows:

TABLE 1
PHYSICAL PROPERTIES OF SELECTED FLUOROCARBONS

| | | "FREON.11" CCl$_3$F | "FREON.12" CCl$_2$F$_2$ | "FREON.21" CHCl$_2$F | "FREON.22" CHClF$_2$ | "FREON.114" CHClF$_2$—CClF$_2$ | "FREON.115" CClF$_2$—CF$_3$ | FREON-113 CCl$_2$F CClF$_3$ |
|---|---|---|---|---|---|---|---|---|
| Chemical Formula | | | | | | | | |
| Molecular Weight | | 137.38 | 120.93 | 102.93 | 86.48 | 170.93 | 154.48 | 187.38 |
| Boiling Point at 1 atm. | °C. | 23.77 | −29.79 | 8.92 | −40.80 | 3.55 | −38.7 | 47.57 |
| | °F. | 74.78 | −21.62 | 48.06 | −41.44 | 38.39 | −37.7 | 117.63 |
| Freezing Point | °C. | −111 | −158 | −135 | −160 | −94 | −106 | −35 |
| | °F. | −168 | −252 | −211 | −256 | −137 | −159 | −31 |
| Critical Temperature | °C. | 198.0 | 112.0 | 178.5 | 96.0 | 145.7 | 80.0 | 214.1 |
| | °F. | 388.4 | 233.6 | 353.3 | 204.8 | 294.3 | 175.9 | 417.4 |
| Critical Pressure | atm. | 43.2 | 40.6 | 51.0 | 48.7 | 32.1 | 30.8 | 33.7 |
| | lbs/sq in abs | 635 | 596.9 | 750 | 716 | 474 | 453 | 495 |
| Critical Volume | cc/mol | 247 | 217 | 197 | 164 | 293 | 259 | 325 |
| Critical Density | g/cc | 0.0289 | 0.0287 | 0.0307 | 0.0305 | 0.0275 | 0.0269 | 0.0278 |
| | lbs/cu ft | 0.554 | 0.558 | 0.522 | 0.525 | 0.582 | 0.596 | 0.576 |
| Density, Liquid | | 34.6 | 34.8 | 32.6 | 32.8 | 36.3 | 37.2 | 36.0 |
| at 30° C. | g/cc | 1.464 | 1.292 | 1.354 | 1.175 | 1.440 | 1.265 | 1.565 |
| at 86° F. | lbs/cu ft | 91.38 | 80.67 | 84.52 | 73.36 | 89.91 | 78.99 | 97.69 |
| at 25° C. (77° F.) | g/cc | | | | | | | 1.49 |
| | lbs/cu ft | | | | | | | 93.01 |
| at 54.5° C. (130° F.) | g/cc | | | | | | | |
| | lbs/cu ft | | | | | | | |
| Density, Sat'd Vapor at b.p. | g/l | 5.85 | 6.33 | 4.57 | 4.82 | 7.82 | 8.37 | 7.38 |
| | lbs/cu ft | 0.365 | 0.395 | 0.285 | 0.301 | 0.488 | 0.522 | 0.461 |
| Specific Heat, Liquid (Heat Capacity) | | | | | | | | |
| at 30° C. | cal/(g)(°C.) | 0.209 | 0.240 | 0.256 | 0.335 | 0.238 | 0.285 | |
| at 86° F. | Btu/(lb)(°F.) | | | | | | | |
| at 25° C. (77° F.) | | | | | | | | 0.218 |
| Specific Heat, Vapor, at Const. Pressure (Heat Capacity) ++ (1 atm.) | | | | | | | | |
| at 30° C. | cal/(g)(°C.) | | | | | | | |
| at 86° F. | Btu/(lb)(°F.) | | | | | | | |
| at 25° C. (77° F.) | cal/(g)(°C.) | 0.135 | 0.145 | 0.140 | 0.152 | 0.160 | 0.164 | |
| | Btu/(lb)(°F.) | | | | | | | |
| Specific Heat Ratio of Vapor at 25° C. and 1 atm | Cp/Cv | 1.136 | 1.137 | 1.175 | 1.184 | 1.088 | 1.091 | |
| Specific Heat Ratio, at 30° C. and 1 atm. (Cp/Cv)+ | | | | | | | | |
| Heat of Vaporization at b.p. | cal/g | 43.51 | 39.47 | 57.86 | 55.92 | 32.78 | 30.11 | |
| | Btu/lb | 78.31 | 71.04 | 104.15 | 100.66 | 59.00 | 54.20 | |
| Thermal Conductivity at 30° C. or 86° F. | | | | | | | | |
| Liquid | Btu per (hr)(sq ft)(°F. per ft) | 0.0609 | 0.0492 | 0.0697 | 0.0595 | 0.0447 | | 0.0434 |
| Vapor (1 atm.) | Btu per (hr)(sq ft)(°F. per ft) | 0.00484 | 0.00557 | 0.00569 | 0.00678 | 0.00646 | | 0.0044 |
| Thermal Conductivity at 25° C. (77° F.) | | | | | | | | |
| Liquid | Btu per (hr)(ft)(°F.) | | | | | | | (0.5 atm) |
| Vapor (1 atm) | | | | | | | | |
| Date from ASHRAE in most cases | | | | | | | 0.161 @ 60° C. (140° F.) | |
| | | | | | | | 1.080 @ 60° C. (140° F.) | |
| Viscosity at 30° C. or 86° F. | | | | | | | | |
| Liquid | centipoise | 0.405 | 0.251 | 0.330 | 0.229 | 0.356 | | |

TABLE 1-continued

PHYSICAL PROPERTIES OF SELECTED FLUOROCARBONS

| | | "FREON.11" CCl$_3$F | "FREON.12" CCl$_2$F$_2$ | "FREON.21" CHCl$_2$F | "FREON.22" CHClF$_2$ | "FREON.114" CHClF$_2$—CClF$_2$ | "FREON.115" CClF$_2$—CF$_3$ | FREON-113 CClF$_2$CClF$_3$ |
|---|---|---|---|---|---|---|---|---|
| Chemical Formula | | | | | | | | |
| Vapor (1 atm.) | | | | | | | | |
| Viscosity at 25° C. (77° F.) | centipoise | 0.0111 | 0.0127 | 0.0116 | 0.0131 | 0.0117 | | |
| Liquid | centipoise | | | | | | | 0.68 |
| Vapor (1 atm) | centipoise | | | | | | | 0.010 |
| | | | | | | | | 0.1 atm |
| Surface Tension at 25° C. or 77° F. | dynes/cm | 19 | 9 | 19 | 9 | 13 | | 17.3 |
| Refractive Index of Liq. | n$_D$26.3° C. | 1.384 | 1.285 | 1.361 | 1.252 | 1.290 | | |
| Refractive Index of Liquid at 25° C. (77° F.) | | | | | | | 2.8 | 1.354 |
| Relative Dielectric Strength at 1 atm and 23° C. (nitrogen = 1) | | 3.1 | 2.4 | 1.3 | 1.3 | 2.8 | | |
| Relative Dielectric Strength of Vapor at 1 atm and 25° C. (77° F.) (nitrogen = 1) | | | | | | | | 3.9 (0.44 atm) |
| Dielectric Constant | | | | | | | | |
| Liquid | temp. in °C. | 2.28$^{29}$ | 2.13$^{29}$ | 5.34$^{28}$ | 6.11$^{24}$ | 2.17$^{31}$ | | 2.41 @ |
| Vapor (0.5 atm.) | temp. in °C. | 1.0019$^{26}$ | 1.0016$^{29}$ | 1.0035$^{30}$ | 1.0035$^{25.4}$ | 1.0021$^{26.8}$ | 1.0018$^{27.4}$ | 25° C. |
| Solubility of "Freon" in Water at 1 atm. and 25° C. (77° F.) | wt. % | 0.11 | 0.028 | 0.95 | 0.30 | 0.013 | 0.006 | 0.017 (Sat'n Pres) |
| Solubility of Water in "Freon" | | | | | | | | |
| at 30° C. (86° F.) | wt. % | 0.013 | 0.012 | 0.16 | 0.15 | 0.011 | | |
| at 0° C. (32° F.) | 1.% 0.0036 | 0.0026 | 0.055 | 0.060 | 0.0026 | | | 0.011 |
| at 25° C. (77° F.) | wt.% | | | | | | | |
| Solubility Parameter ( ) | | | | | | | | 72 |
| Kauri Butanol Value (KB) | | | | | | | | 32 |
| Toxicity$^a$ | ppm(v/o) | | | | | | | 1000 |
| Threshold Limit Value (TLV) | mg/m$^3$ | | | | | | | 7600 |
| Flammability | | nonflammable | nonflammable | nonflammable | nonflammable | nonflammable | nonflammable | |
| Toxicity | | Group 5A+ | Group 6+ | much less than Group 4. somewhat more than Group 5+ | Group 5A+ | Group 6+ | probably Group 6 | |
| Vapor Pressure at 21° C. PSI absolute | | 13 | 83 | 23 | 150 | 28 | 120 | |
| Kauri-Butanol Number | | 60 | 18 | 102 | 25 | 12 | — | |

Referring again to FIG. 1, compressor 35 pumps extraction solvent 47 into extractor injection units 32 and pulls a reduced pressure in the extraction separation unit 14 which vaporizes extraction solvent 47 at nozzle 40 to deposit mixture 48, which contains n-butanol in the bottom of unit 14 where it is periodically removed via pipe line 50 and valve 49. Condenser 41 cools the extraction solvent vapors so that solvent 47 is delivered to standing pipe 33 as a liquid.

The extracted liquor passes out of the top of extractor unit 12 into pipe line 38 to feed tank 13 where additional feed material is added to the liquor via valve 39. Feed tank 13 is equipped with mixture 53 which has agitators 54 to conveniently mix recycled liquor 42 with the new feed material. Carbon dioxide and other gases are generated by the fermentation. These gases are controllably exhausted from reactor 11 by means of pipe line 51 and control pressure valve 52. Reactor 11 is equipped with drain 55 in order to selectively or completely remove the contents thereof.

Compressor 35 is operated at a rate sufficiently high to provide enough extraction solvent 47 to completely remove all of the butanol from the liquor. This rate is dependent upon the pass rate of liquor through the reactor system.

The cylindrical design of reactor 11 is advantageous in the continuous fermentation process. One advantage results from the fact that the velocity of recycled liquor 42 is highest when it enters region 43 where the culture is present. At that point in reactor 11 there is little fermentation product to inhibit the fermentation and reduce the fermentation rate and the concentration of the substrate is highest vis-a-vis any other point in reactor 11. Thus, reaction proceeds at a high rate. As the liquor moves outward, the velocity decreases, the cross section of available culture increases, and the reaction is continued at a high rate because of the longer residence time and the larger number of bacilli operating on the liquor which compensates for the inhibiting action of the fermentation products produced. The result is an efficient fermentation conversion.

There is another advantage to the preferred cylindrical shape of reactor 11. At the point where the liquor passes through membrane filter 22, the velocity is very low compared with the entrance velocity at central distribution pipe 18. This avoids the difficulty of clogging filter medium 23 by having the fluid pass through at high rates.

Figure 7:
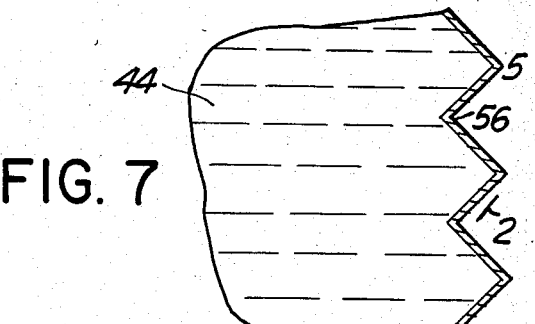
FIG. 7 is a plan view of FIG. 6.

Clogging may also be reduced by the use of a scraper unit against the inner wall of membrane wall 22 and also by the introduction of a pulsating pressure at sonic to ultra sonic frequencies into space 46 by the use of conventional transducers. The problem associated with clogging of filter medium 23, i.e., decreased flow through filter medium 23, may also be overcome by increasing the area of the membrane wall. One means of accomplishing this is illustrated in FIG. 7 where membrane wall 22 is pleated at points 56 and 58. This pleated structure substantially increases the area of the membrane wall and reduces the pressure drop caused by the flow. This construction may be used with parallel plate constructions of the reactor that would be suitable for some applications.

Figure 9:
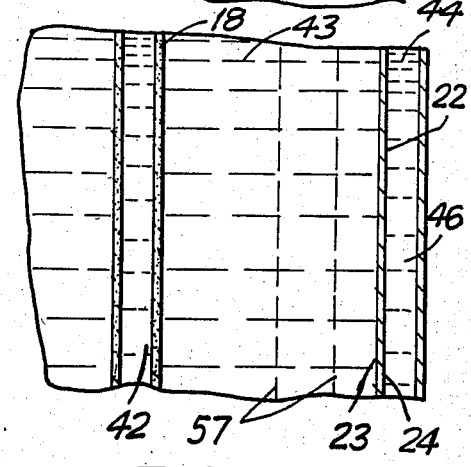
FIG. 9 is a partial section of the main reactor body with additional membranes.

Certain culture variations of the bacteria act at different stages in the fermentation process for converting the carbohydrate-containing substrate to butanol. In order to improve the rate and efficiency of operation of the fermentation unit, it may be desirable to segregate these different types of cultures in reactor 11. This may be accomplished by employing membranes similar to membrane 22, but having different pore sizes to suit the particular circumstances. This arrangement is shown in FIG. 9 by membranes 57.

The apparatus used in the fermentation system described herein may be made with a variety of materials. These materials should not be affected by the fermentation process or by the fermentation products. Reactor 11 and other equipment may be made, for example, from steel, stainless steel, aluminum, polyvinyl chloride, polyethylene, and other resistant polymers. The porous pipe may be made from sintered stainless steel, bronze, aluminum, or other materials known to those skilled in this art. The membrane filter material may be made, for example, from cellulose fiber and may be essentially a filter paper. It may also be made from a synthetic fiber paper using polyester or polypropylene fibers. Furthermore, certain filter membranes are made of polyvinyl chloride and of polypropylene. These membranes are made with pores in the range of from about 0.1 to about 2 microns, which is the normal size range for the bacteria spores. Other filter materials, well known to those skilled in this art, may also be used as the filter material. The particular pore size of the filter material depends upon the culture employed and may be readily determined by those skilled in this art.

The materials of construction for the other portions of the apparatus of the fermentation system described herein are metals which are conventionally used in chemical processing equipment.

Other additives may be used in reactor 11 in order to, for example, adjust the pH of the system to enhance fermentation. Typical additives to control pH include calcium hydroxide, calcium carbonate, and dilute solutions of sulfuric acid. The usual amount of calcium carbonate is from about 5 to about 7 percent by weight of the substrate.

Nutrients, such as amino acid-containing substances, may also be added to reactor 11. Ethyl grain, butyl grain, and molasses stillages may be used to buffer the fermentation mass and serve as a source of nutrients. The use of stillage results in better yields. Other additives to increase yield and control the fermentation rate are set forth in Chapter 13 of *Industrial Microbiology* (McGraw Hill 1959).

The fermentation reaction requires certain conditions. The optimum fermentation temperature is 31° C. Although the pH may vary from about 5 to about 7, the initial pH is usually from about 5.5 to about 6.5 while the final pH is typically from about 5.2 to 6.2. Since the fermentation is anaerobic, it may be advantageous to maintain sterile carbon dioxide at a pressure until the bacteria have had an opportunity to build up a pressure of their own.

The cultures in reactor 11 are preferably contained in a fixed bed. The tendency of n-butanol in sufficiently high concentrations to inhibit the fermentation reaction is reduced by the presence of the filter member which effectively removes the n-butanol from the culture shortly after production.

The present invention is further illustrated by the following examples. All parts and percentage in the examples as well as in the specification and claims are by weight unless otherwise specified.

EXAMPLE 1

Maize or other similar carbohydrate material is ground to a coarse meal which is then mixed with sufficient water to give approximately an 8% by weight concentration of maize. If desired, the corn germ and a portion of the bran may be removed prior to mashing. The resulting mixture of maize meal and water is introduced into pressure cookers provided with suitable agitators, where it is heated with live steam at approximately thirty pounds pressure for two hours. This operation serves both to thoroughly sterilize the mash and at the same convert the starch of the maize into a form more easily acted upon by the bacteria.

Two "cooks" of mash consisting of about 5,600 gallons each, prepared in the manner described above, are cooled to approximately 37° C. and then introduced into reactor 11 which has previously been thoroughly sterilized. The mash is next inoculated with a culture of butylacetonic bacillus, preferably *Clostridium acetobutyicum* (Weizmann). The amount of inoculum may vary, but it is generally preferred to use about 2% by volume. At subsequent intervals of about four hours, additional mash is added in lots of either one or two "cooks" (consisting of about 5,600 gallons each) until reaction 11 contains a total of seven "cooks." It is thus seen that twelve hours or more time must elapse before reactor 11 reaches its maximum fermenting capacity. A normal fermentation is usually completed in approximately 52 hours from the time of inoculation. During the course of the fermentation, abundant quantities of hydrogen and carbon dioxide gases are liberated and solvents in approximately the ratio of six parts of n-butanol, three parts of acetone and one part of ethyl alcohol are formed.

Further details of the fermentation process, including substrates, cultures, etc. are set forth in U.S. Pat. No. 1,875,536, the disclosure of which is hereby incorporated by reference.

At the conclusion of the fermentation, the product mixture is extracted with the fluorocarbon solvent. The specific fluorocarbon solvent which works best with n-butanol is FREON-11 or F-11 (monofluoro trichloro methane). Using a countercurrent extraction, the residual butanol may be reduced to less than 0.004% by contacting finally with pure F-11.

The F-11 is evaporated by applying a vacuum to the container in which the solution of n-butanol in F-11 is contained. The F-11 boiling point of 23.8° C. at one atmosphere is raised by the pressure produced by the n-butanol, but the F-11 will boil at room temperature at reduced pressures. The heat required to do this is supplied from the external environment and the driving force is the pump that creates the vacuum.

One of the main applications of interest for the butanol produced from the present process is for use as a fuel. The extraction efficiency may be determined as follows:

extraction efficiency =

$$\frac{\text{Heat of combustion} - \text{Heat of extraction}}{\text{Heat of combustion}} \times 100$$

For the extraction of n-butanol using, for example, three (3) parts by weight of F-11 per part of butanol, the theoretical extraction efficiency would be $$\frac{8630 - 3 \times 43.51}{8630} \times 100 = 98.49\%$$

This theoretical value represents the efficiency without regeneration, i.e., the heat generated by recompressing the fluid is used to improve the evaporation, in which case less energy would be required. While this theoretical calculation does not take into account the inefficiency in the system, it nevertheless shows the relatively high thermal efficiency of the present process using the F-11 extraction solvent for extracting n-butanol.

EXAMPLE 2

Example 1 is re-run, but at the conclusion of the fermentation, the product mixture is extracted with FREON-12 or F-12 (dichloro difluoro methane) and similar results are obtained.

EXAMPLE 3

Example 1 is re-run, but at the conclusion of the fermentation, the product mixture is extracted with FREON-21 or F-21 (monofluoro dichloro methane) and similar results are obtained.

EXAMPLE 4

Example 1 is re-run, but at the conclusion of the fermentation, the product mixture is extracted with FREON-22 or F-22 (difluoro monochloro methane) and similar results are obtained.

EXAMPLE 5

Example 1 is re-run, and at the conclusion of the fermentation, the product mixture is extracted with FREON-114 or F-114 (dichloro tetrafluoro ethane) and similar results are obtained.

EXAMPLE 6

Example 1 is re-run, but at the conclusion of the fermentation, the product mixture is extracted with FREON-115 or F-115 (pentafluoro monochloro ethane) and similar results are obtained.

EXAMPLE 7

Example 1 is re-run, but at the conclusion of the fermentation, the product mixture is extracted with FREON-113 or F-113 (1,1,2-trichloro, 1,2,2-trifluoro ethane) and similar results are obtained.

There are many additional examples of fluorocarbons which may be used as the extraction solvents which are similar to those listed in Table 1, some of which are not in commercial production and for which there is no data available concerning the vapor pressure, solvency, and the other data required to determine the efficiency in this type of extraction process or the operating temperature and pressure required. It is intended that such compounds be regarded as embodiments of the present invention if their physical constants fall within the range of those specifically recited.

As shown in Table 1, numerous combinations of fluorocarbon solvents are possible for the solvent system. The operating conditions with respect to temperature, pressure, and concentrations of the solute alcohol in the initial entry stream, the extract, and the raffinate may vary without departing from the intent and the spirit of the invention. These variables may be adjusted to suit the specific requirements of the particular extraction installation in a manner well known to those skilled in the art. These choices of operating parameters may be made without departing from the spirit and scope of the present invention.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

I claim:

1. A continuous process for the production of n-butanol from the starting materials of an anaerobic fermentation process comprising:
   (a) continuously contacting at least one carbohydrate-containing substrate with an n-butanol producing culture in water to effect the fermentation of substrate and form a product mixture comprising n-butanol,
   (b) continuously extracting said product mixture from said substrate, said culture and said water by forming a solution of said product mixture with an extraction solvent while substantially avoiding the formation of a solution of said solvent with said substrate, said culture, and said water, wherein said extraction solvent is at least one fluorocarbon solvent selected from the group consisting of fluorocarbons that boil at temperatures between −41° C. and +48° C., have vapor pressures at 21° C. between 10 PSIA and 165 PSIA, have heats of vaporization below 60 calories per gram, have a specific heat below 0.28, have a surface tension below 20 dynes per centimeter, have a viscosity below 0.5 centipoise, have a solubility below 1% in water, and have a solubility below 0.2% of water in the fluorocarbon,
   (c) continuously separating said extraction solvent from said product mixture by vaporizing substantially all of said solvent without substantial vaporization of said product mixture, and
   (d) continuously condensing said vaporized solvent for reuse as an extraction solvent in step (b).

2. The process of claim 1 wherein said culture is of the genus Clostridium.

3. The process of claim 2 wherein said culture is *Clostridium acetobutylicum* (Weizmann).

4. The process of claim 1 wherein said substrate is a mash of starched materials derived from corn, wheat, oats, and other grain materials.

5. The process of claim 1 wherein said substrate is at least one member selected from the group consisting of beet molasses, blackstrap molasses, citrus molasses, invert sugar, sucrose, fructose, glucose, wood sugar and xylose.

6. The process of claim 1 wherein said extraction solvent is a fluorocarbon containing one or two carbon atoms and from one to six fluorine atoms with the remainder being hydrogen and chlorine.

7. The process of claim 1 wherein said extraction solvent is difluorodichloromethane.

8. The process of claim 1 wherein said extraction solvent is monofluorodichloromethane.

9. The process of claim 1 wherein said extraction solvent is difluoromonochloromethane.

10. The process of claim 1 wherein said extraction solvent is dichlorotetrafluoroethane.

11. The process of claim 1 wherein said extraction solvent is pentafluoromonochloroethane.

12. The process of claim 1 wherein said extraction solvent is 1,1,2-trichloro-1,1,2-trifluoroethane.

13. The process of claim 1 wherein said product mixture is separated from said culture prior to extraction step (b).

14. The process of claim 1 wherein said fermentation is conducted stepwise by different strains of bacteria.

15. A continuous process for the production of n-butanol from the starting materials of an anaerobic fermentation process comprising:
   (a) continuously contacting a blackstrap molasses substrate with an effective amount of *Clostridium acetobutylicum* (Weizmann) culture in water to effect the fermentation of said substrate and form a product mixture comprising n-butanol,
   (b) continuously extracting said product mixture from said substrate and said culture by forming a solution of said product mixture with an extraction solvent, while substantially avoiding the formation of a solution of said solvent with said substrate, said culture, and said water, wherein said extraction solvent is a fluorocarbon containing one or two carbon atoms and from one to six fluorine atoms with the remainder being hydrogen and chlorine,
   (c) continuously separating said extraction solvent from said product mixture by vaporizing substantially all of said solvent without substantial vaporization of said product mixture, and
   (d) continuously condensing said vaporized solvent for reuse as an extraction solvent in step (b).

* * * * *